(12) United States Patent
Mantovani et al.

(10) Patent No.: US 11,185,415 B2
(45) Date of Patent: Nov. 30, 2021

(54) MOULD FOR REALIZING A TEMPORARY PROSTHESIS OF HIP OR SHOULDER, AND METHOD THEREOF

(71) Applicant: G21 S.R.L., San Possidonio (IT)

(72) Inventors: Matteo Mantovani, Carpi (IT); Daniele Baetta, Carpi (IT)

(73) Assignee: G21 S.R.L., San Possidonio (IT)

(*) Notice: Subject to any disclaimer, the term of this patent is extended or adjusted under 35 U.S.C. 154(b) by 568 days.

(21) Appl. No.: 16/068,571

(22) PCT Filed: Jan. 10, 2017

(86) PCT No.: PCT/IB2017/050111
§ 371 (c)(1),
(2) Date: Jul. 6, 2018

(87) PCT Pub. No.: WO2017/125832
PCT Pub. Date: Jul. 27, 2017

(65) Prior Publication Data
US 2019/0015210 A1  Jan. 17, 2019

(30) Foreign Application Priority Data
Jan. 19, 2016 (IT) ................. 102016000004228

(51) Int. Cl.
*A61F 2/30* (2006.01)
*A61F 2/36* (2006.01)
(Continued)

(52) U.S. Cl.
CPC .............. *A61F 2/30* (2013.01); *A61F 2/3094* (2013.01); *A61F 2/36* (2013.01); *A61F 2/4059* (2013.01);
(Continued)

(58) Field of Classification Search
CPC .............. A61F 2/30; A61F 2002/30975; A61F 2002/30672; B29C 45/14065; B29K 2033/12
See application file for complete search history.

(56) References Cited

U.S. PATENT DOCUMENTS 7,789,646 B2   9/2010  Haney et al.
8,480,389 B2   7/2013  Haney et al.
(Continued)

FOREIGN PATENT DOCUMENTS

CN   202497267 U   10/2012
CN   203619725 U    6/2014
(Continued)

*Primary Examiner* — Michael M. Robinson
(74) *Attorney, Agent, or Firm* — Pearne & Gordon LLP

(57) ABSTRACT

Mould and method for realizing a temporary prosthesis of hip or shoulder, which comprises a shaft and a head. The mould comprises: a first mould portion (1) comprising a first half-shell (2); a second mould portion (3) comprising a second half-shell (4); the first mould portion (1) and the second mould portion (3) being able to be coupled with respect to each other so that the first and second half-shell (2, 4) are counter-faced and define a chamber (5) which conforms a shaft portion (5a), a head portion (5b) and an opening (5c) for injection of a fluid (preferably viscous) material; fixing means (6) for fixing the first and the second portion (1, 3); a first insert (7) comprising a cap portion (8) which is realized as a unique body, is dimensioned to be inserted in the head portion (5b) and is conformed to give shape to the head of the prosthesis. The first mould portion (1), the second mould portion (3) and the first insert (7) are mutually conformed to obtain a temporary prosthesis, when the first mould portion (1) and the second mould portion (3) are coupled together, the first insert (7) is inserted in the head portion (5b) and the fluid (preferably viscous) material is injected in the opening (5c).

10 Claims, 7 Drawing Sheets

(51) Int. Cl.
  *A61F 2/40*    (2006.01)
  *B29C 45/14*   (2006.01)
  *B29K 33/00*   (2006.01)
  *B29L 31/00*   (2006.01)

(52) U.S. Cl.
  CPC .......... *B29C 45/14065* (2013.01); *A61F 2002/30616* (2013.01); *A61F 2002/30672* (2013.01); *A61F 2002/30975* (2013.01); *A61F 2002/3611* (2013.01); *A61F 2002/4018* (2013.01); *A61F 2310/00353* (2013.01); *B29C 2045/14131* (2013.01); *B29K 2033/12* (2013.01); *B29K 2823/06* (2013.01); *B29L 2031/7532* (2013.01)

(56) References Cited

U.S. PATENT DOCUMENTS

| | | |
|---|---|---|
| 8,801,983 B2 | 8/2014 | Haney et al. |
| 9,937,047 B2 | 4/2018 | Holt et al. |
| 2009/0146342 A1 | 6/2009 | Haney et al. |
| 2010/0297276 A1 | 11/2010 | Haney et al. |
| 2013/0344186 A1 | 12/2013 | Haney et al. |
| 2014/0348973 A1* | 11/2014 | Holt ............ B29C 48/03 425/542 |
| 2016/0332328 A1 | 11/2016 | Wüst et al. |

FOREIGN PATENT DOCUMENTS

| | | |
|---|---|---|
| EP | 3075357 A1 | 10/2016 |
| WO | 2009073781 A2 | 6/2009 |
| WO | 2013086177 A1 | 6/2013 |

\* cited by examiner

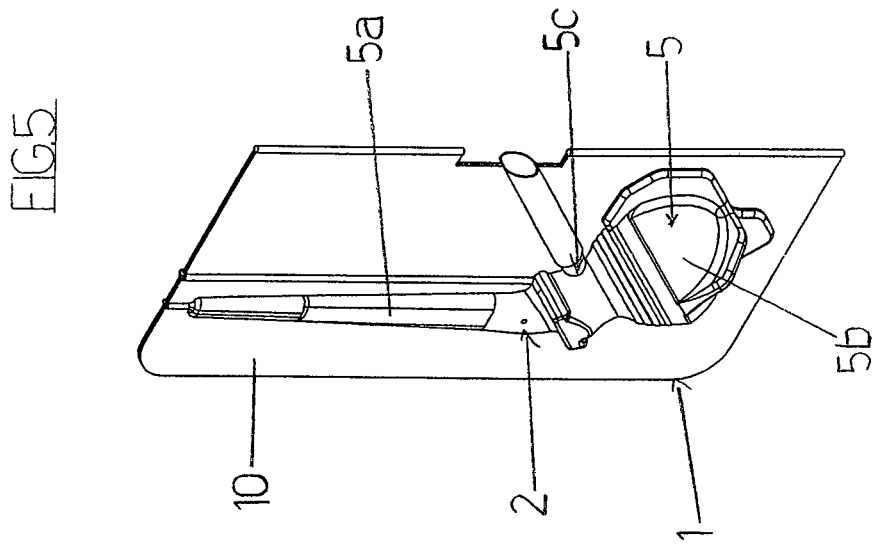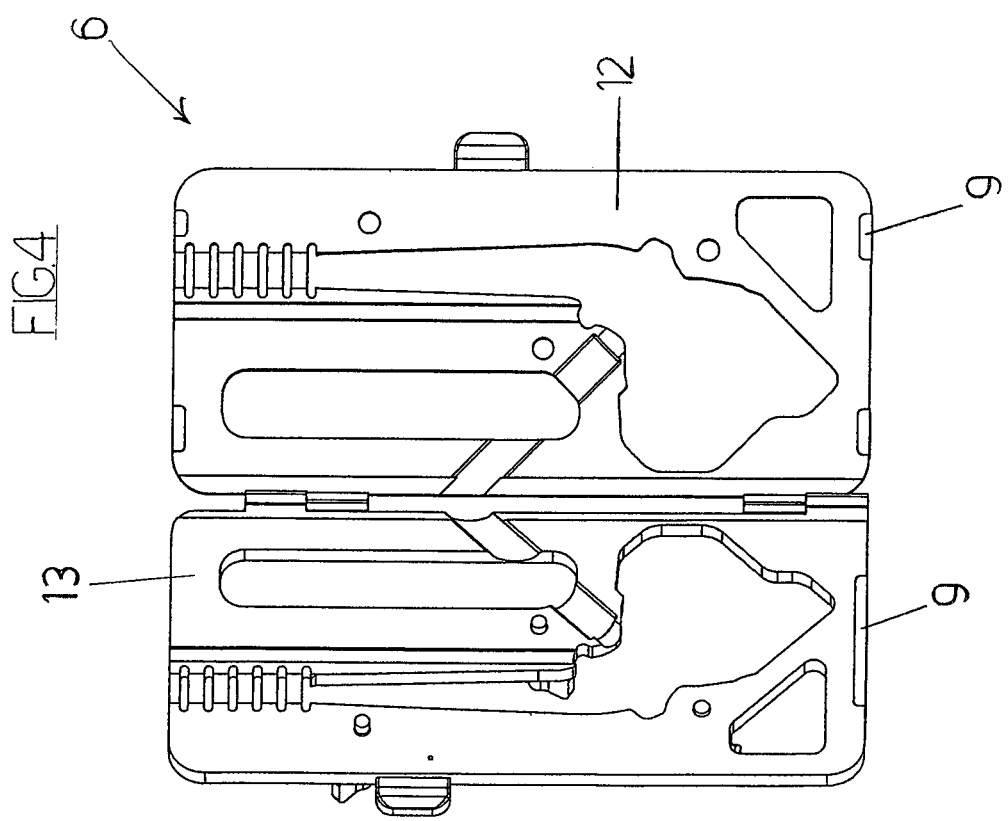

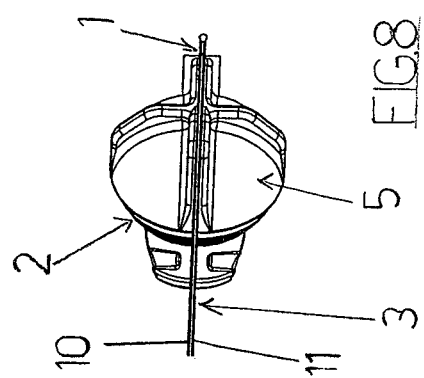
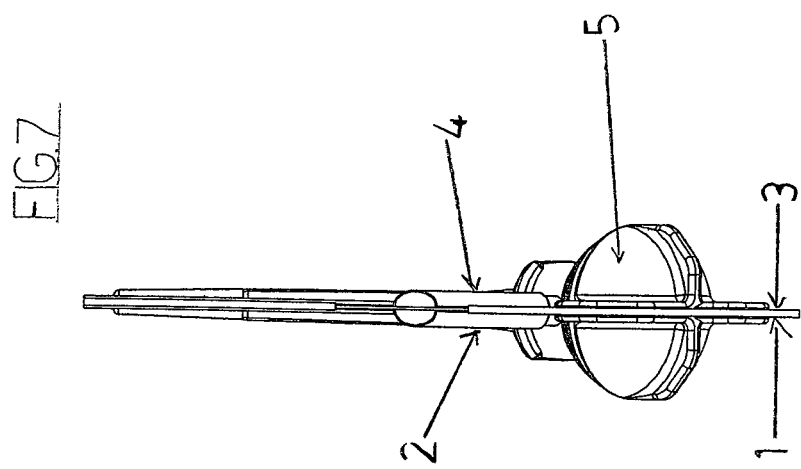
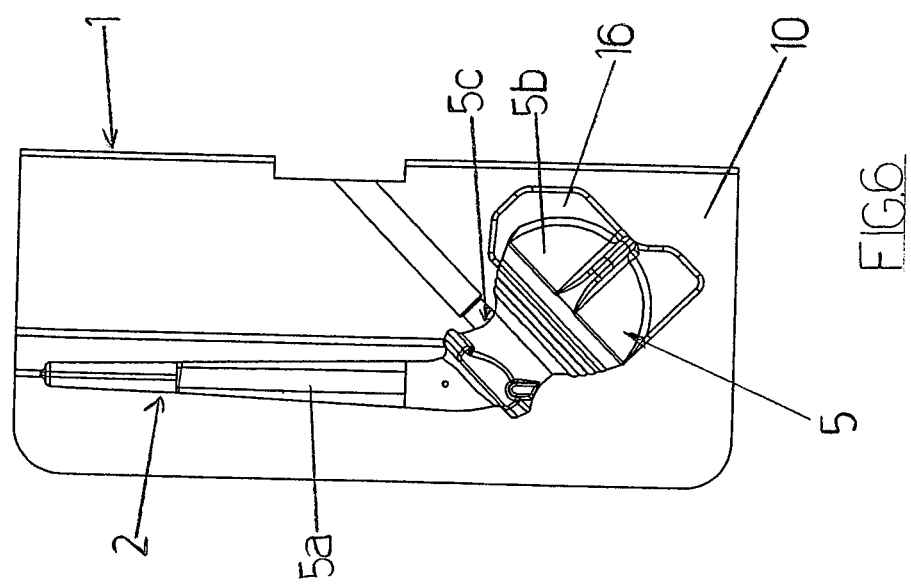

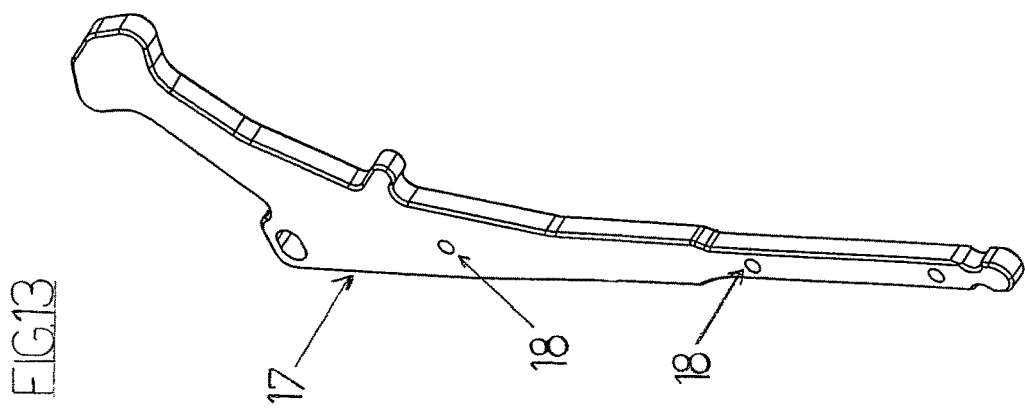
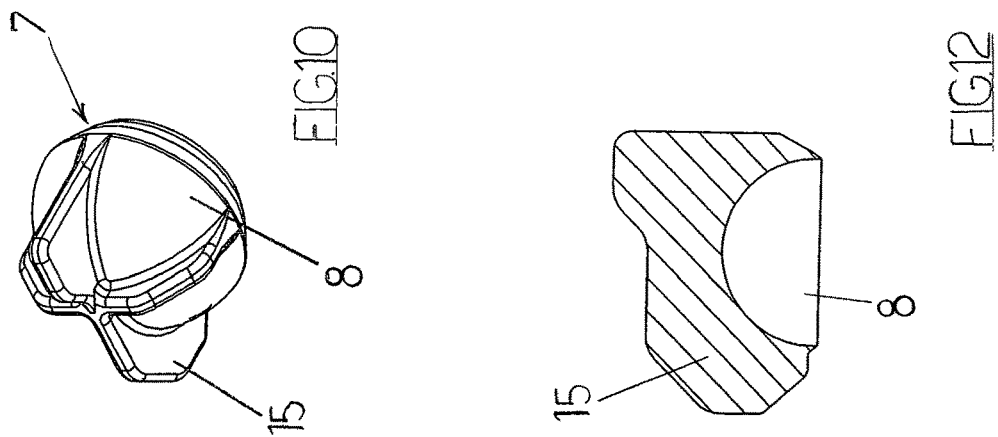
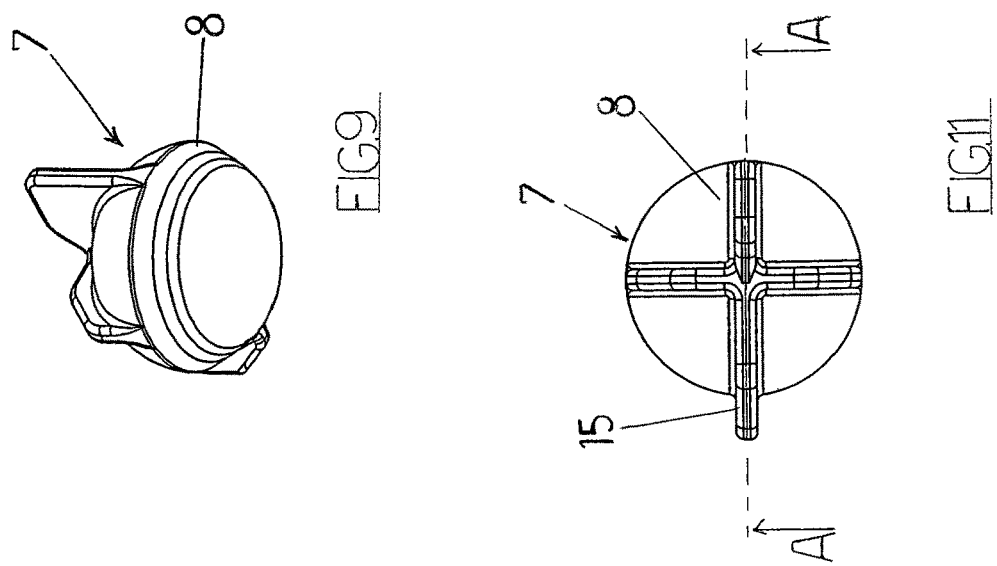

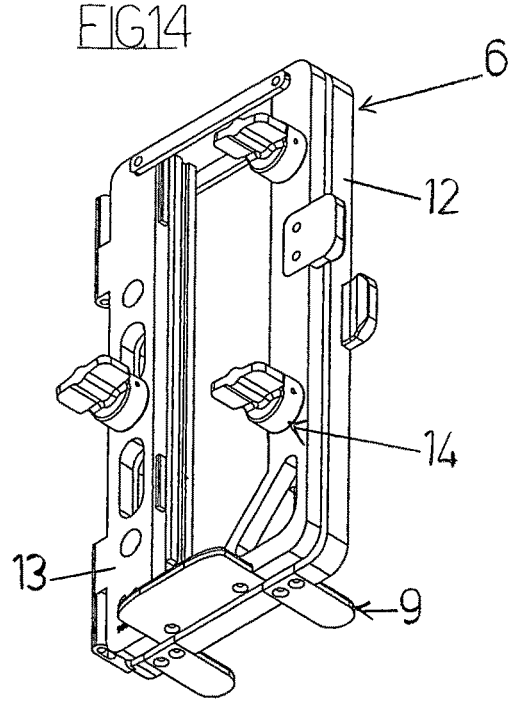
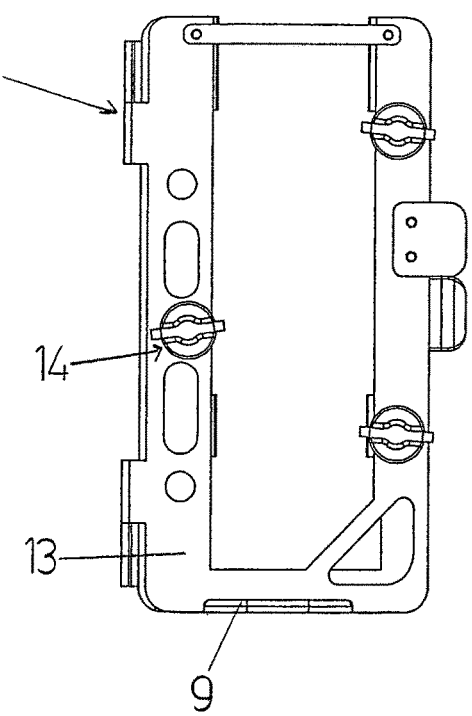
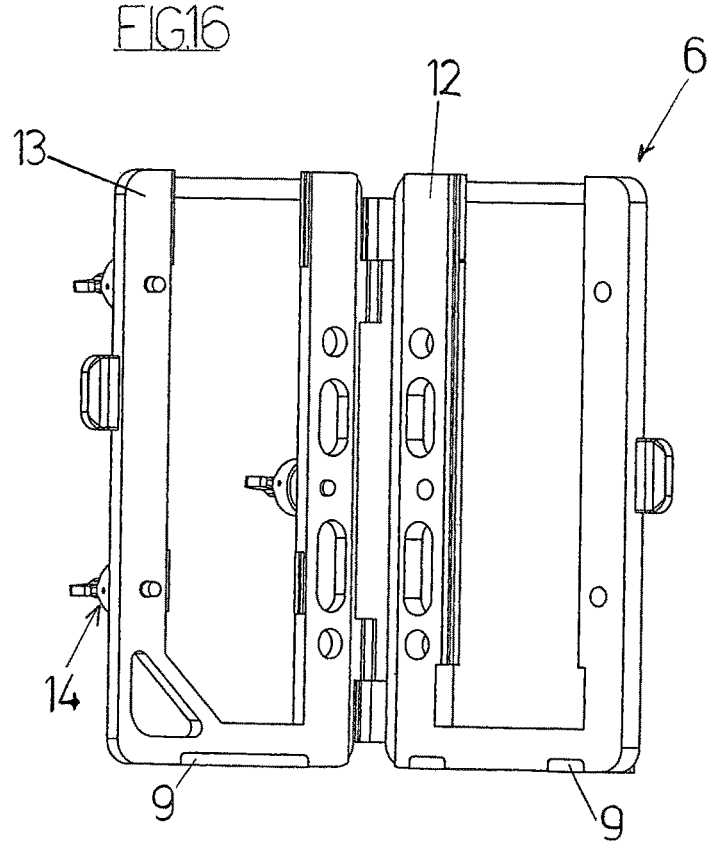

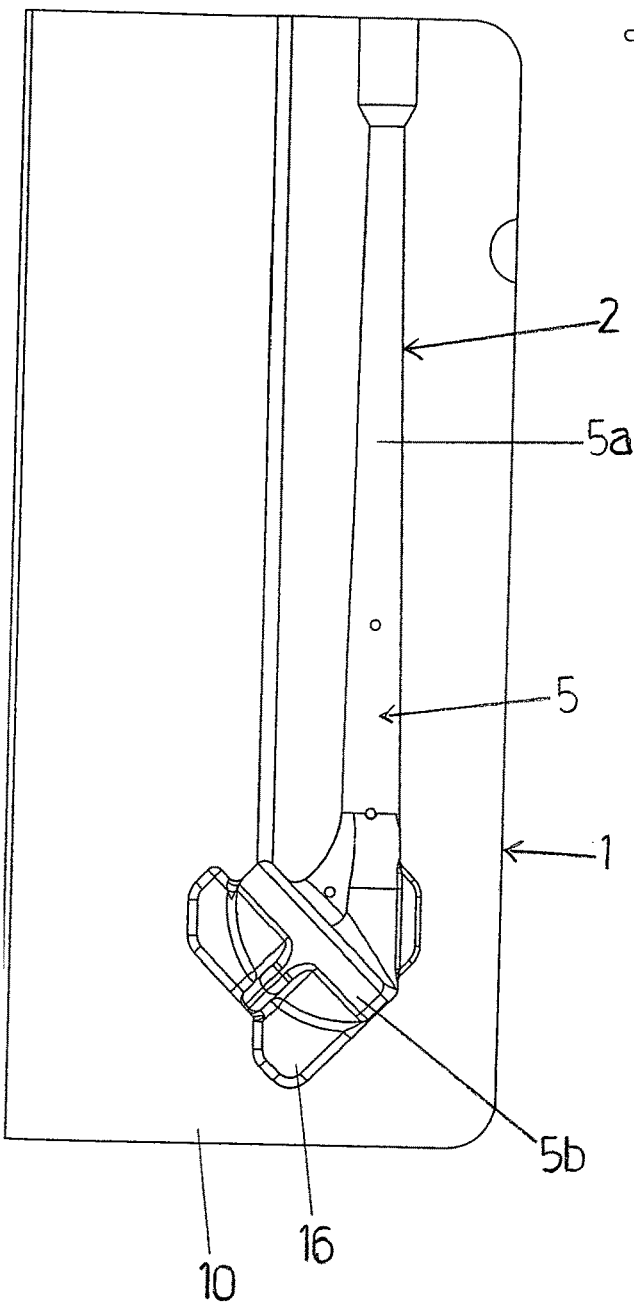
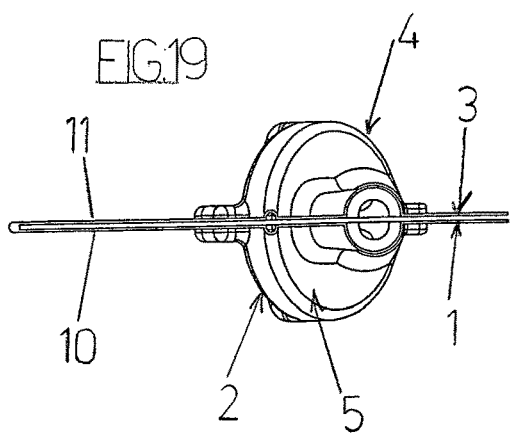
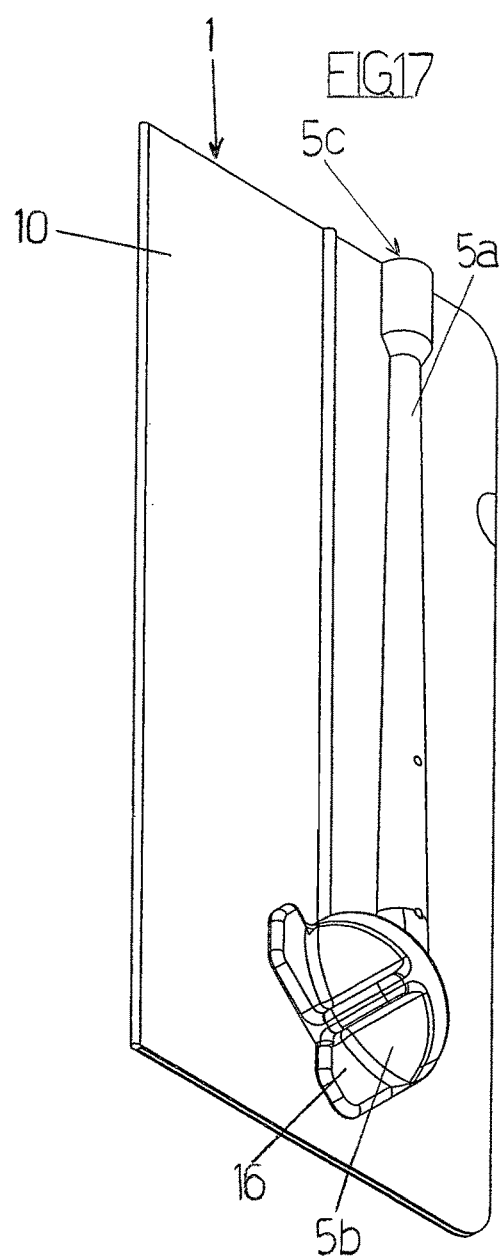

MOULD FOR REALIZING A TEMPORARY PROSTHESIS OF HIP OR SHOULDER, AND METHOD THEREOF

FIELD OF THE INVENTION

The present invention relates to the technical field of the temporary prosthesis of hip or shoulder. In particular, the present invention relates to a mould for realizing a temporary prosthesis of hip or shoulder and a method thereof. Yet, the invention relates to a mould usable during the implantation surgical procedure of a temporary prosthesis of hip or shoulder.

STATE OF THE ART

A temporary prosthesis (also called spacer) is a medical device used in the infections treatment of joint prostheses. In particular, in case of a patient with an infected definitive prosthesis, the surgeon proceeds to the removal of the infected definitive prosthesis, to tissues surgical cleaning and to the positioning of a temporary prosthesis. Said temporary prosthesis, usually realized in bone cement and able to release antibiotics, is held implanted for some months to cure the infection. In the following, the surgeon proceeds to the removal of the temporary prosthesis, to tissues surgical cleaning again and to the implantation of a new definitive prosthesis.

A prosthesis of hip or shoulder, whether temporary or definitive, comprises a shaft intended to be implanted inside a bone (for example, in case of hip prosthesis, the shaft is implanted inside the femur) and a head fixed to the shaft which is intended to replace the joint coupling. Therefore, it is mainly the head portion of a prosthesis which defines the tribological performances of the implant. As a consequence, to guarantee good performances of the implant it is important that the head of a prosthesis is compact (i.e. dense, that is free of filling defects and/or recesses) and has good surface finishing.

According to known procedures a temporary prosthesis of hip or shoulder can be realized industrially or in operating rooms during the implantation surgical procedure of the temporary prosthesis of hip or shoulder.

A temporary prosthesis realized industrially (in this case, one talks about preformed temporary prosthesis) has to be ordered by the surgeon weeks before the surgery, according to the X-ray of the patient. However, during the surgery, the surgeon could notice that the ordered temporary prosthesis is not perfectly dimensioned for the patient; in such case, the surgeon has to use said temporary prosthesis anyway, since it is the only one at his disposal. Moreover, the surgeon has limited freedom concerning the antibiotics to choose to be mixed to the bone cement.

To obviate said problems, it is known a mould for realizing a temporary prosthesis of hip or shoulder during the implantation surgical procedure of the temporary prosthesis of hip or shoulder.

Said known mould comprises two half-shells in silicone, which can be couple-restrained between each other, and which, when coupled, define a chamber which conforms a shaft portion, a head portion and an opening for injecting fluid (preferably viscous) bone cement in the same chamber.

Anyway, the temporary prosthesis of hip or shoulder obtained by using a known mould is not provided with a uniform surface: the temporary prosthesis obtained starting from said mould has a surface imperfection at the joint between the two half-shells. Said surface imperfection, even being not a problem for the shaft, is a problem for the head since it determines a reduction in mechanical performances of the temporary prosthesis and as a consequence of the implant.

SUMMARY OF THE INVENTION

Therefore, aim of the present invention is to provide a mould for realizing a temporary prosthesis of hip or shoulder, and a method thereof, which overcomes said drawbacks. In particular, the present mould aims at being usable during the implantation surgical procedure of the same temporary prosthesis and at realizing a temporary prosthesis which is provided with a head and in particular a joint surface with uniform surface.

Said aims are obtained by means of a mould for realizing a temporary prosthesis of hip or shoulder according to claim 1, and a respective method according to claim 8.

Advantageously the mould proposed comprises the first insert which allows to obtain a temporary prosthesis of hip or shoulder having a uniform joint surface.

In particular, the first insert comprises a cap portion which is conformed and designed to give the desired shape to the head of the temporary prosthesis of hip or shoulder. Said cap portion is dimensioned to be introduced in the head portion of the chamber and is realized as a unique body; such features, combined with the conformation of the first mould portion and the second mould portion, allow to obtain the temporary prosthesis of hip or shoulder with uniform joint surface of the head, i.e. regular in shape and with good surface finishing.

Advantageously, the proposed mould is extremely simple and therefore usable during the implantation surgical procedure of the same temporary prosthesis. Moreover, the mould proposed allows to obtain a temporary prosthesis with good mechanical and tribological performances thanks to the surface finishing of the head of the same temporary prosthesis. As a consequence, this guarantees good mechanical and tribological performances of the implant.

BRIEF DESCRIPTION OF THE DRAWINGS

Specific embodiments of the invention will be described in the following according to what claimed and with reference to the appended drawings, in which:

FIG. 4 shows another front view of the fixing means of the first embodiment of the mould;

FIG. 5 shows a perspective view of the first and second mould portion, coupled between each other, of said first embodiment of the mould;

FIGS. 6-8 show a front, side and bottom view of FIG. 5, respectively;

FIG. 9 shows a perspective view of an embodiment of the insert;

FIGS. 10 and 11 show a top perspective view and a top view of the insert of FIG. 9, respectively;

FIG. 12 shows section A-A of FIG. 11;

FIGS. 13 and 24 show different perspective views of embodiments of a stiffening element;

FIGS. 14 and 15 show a perspective view and a side view, respectively, of the fixing means of a second embodiment of the mould object of the present invention;

FIG. 16 shows another front view of the fixing means of the second embodiment of the mould;

FIG. 17 shows a perspective view of the first and second mould portion, coupled between each other, of said second embodiment of the mould;

FIGS. 18 and 19 show a front and bottom view of FIG. 17, respectively;

DESCRIPTION OF PREFERRED EMBODIMENTS

Figure 1:
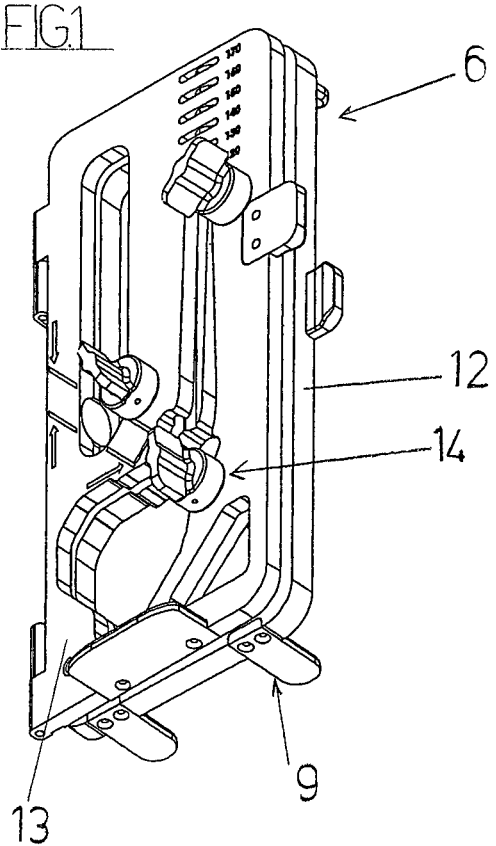
FIG. 1 shows a perspective view of the fixing means of a first embodiment of the mould object of the present invention.
Figure 2:
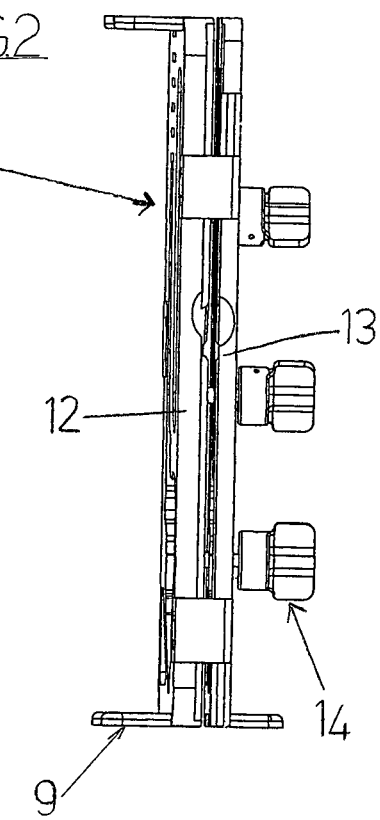
FIGS. 2 and 3 show a side view and a front view of FIG. 1, respectively.
Figure 3:
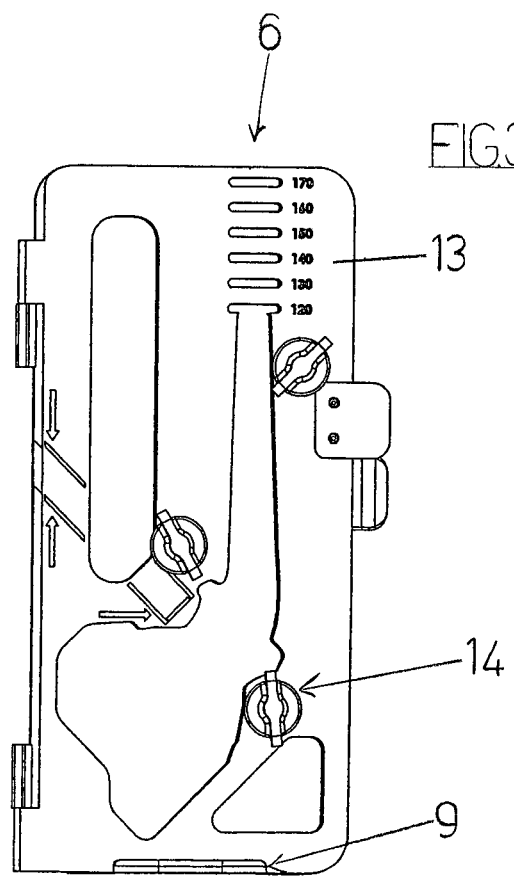

With reference to the appended drawings, FIGS. 1-13 show an embodiment of elements of a mould, object of the present invention, for realizing a temporary prosthesis of hip. Similarly, FIGS. 14-23 show an embodiment of elements of a mould, object of the present invention, for realizing a temporary prosthesis of shoulder.

A temporary prosthesis of hip or shoulder comprises a shaft and a head fixed to the shaft.

The proposed mould comprises a first mould portion (1) comprising a first half-shell (2), and a second mould portion (3) comprising a second half-shell (4). The first mould portion (1) and the second mould portion (3) can be coupled with respect to each other so that, when coupled, the first half-shell (2) and the second half-shell (4) are counter-faced and define a chamber (5) which conforms a shaft portion (5a), a head portion (5b) and an opening (5c) for injection in the same chamber (5) of a suitable fluid (preferably viscous, as for example polymethylmethacrylate) material for a temporary prosthesis of hip or shoulder.

The mould comprises also fixing means (6) for fixing the first mould portion (1) and the second mould portion (3) removably with respect to each other, when the first mould portion (1) and the second mould portion (3) are coupled together.

Moreover, innovatively the mould comprises a first insert (7) comprising a cap portion (8). The cap portion (8) is realized as a unique body, is dimensioned to be inserted in the head portion (5b) of the chamber (5), is in contact to the first half-shell (2) and the second half-shell (4), and is conformed to give the shape to the head of the desired temporary prosthesis of hip or shoulder.

The first mould portion (1), the second mould portion (3) and the first insert (7) are mutually conformed to obtain a temporary prosthesis of hip or shoulder, when the first mould portion (1) and the second mould portion (3) are coupled together, the first insert (7) is inserted in the head portion (5b) of the chamber (5) and the fluid (preferably viscous) material is injected in the opening (5c).

The proposed mould can be used by the surgeon during the implantation surgical procedure of the same temporary prosthesis. Moreover, the use of the first insert (7) allows to obtain a head with a uniform joint surface and this guarantees good mechanical and triboligical performances of the implant.

It is to be précised that the shape of the shaft (5a) is similar to the shape of the shaft of the desired temporary prosthesis of hip or shoulder. Anyway, the shaft portion (5a) can be longer than the shaft of said temporary prosthesis of hip or shoulder desired.

The opening (5c) can be arranged at the head portion (5a) (see FIGS. 5 and 17).

Preferably, the mould comprises supporting means (9) for supporting the first mould portion (1) and the second mould portion (3) when coupled together so that the head portion (5b) is under the shaft portion (5a), so that by adjusting the quantity of fluid (preferably viscous) material injected in the opening (5c) it is possible to set the length of the shaft of the desired temporary prosthesis of hip or shoulder.

Advantageously, this feature allows to increase the mould flexibility. In fact, during the implantation surgical procedure of the temporary prosthesis, a surgeon can adjust the length dimension of the shaft of the desired temporary prosthesis, in loco (i.e. in the operating room).

Moreover, the fact that the head portion (5b) is under the shaft portion (5a) implies that the head portion (5b) is the first to be filled with the fluid (preferably viscous) material injected in the opening (5c). In this way, it is guaranteed a compact head of the temporary prosthesis (and free of possible porosity). As a consequence, advantageously, the mechanical performances of the obtained temporary prosthesis of hip or shoulder results further improved.

In particular, the supporting means (9) can be such that they support the first mould portion (1) and the second mould portion (3), when coupled between each other, so that the shaft portion (5a) is arranged vertically.

With reference to FIGS. 5-8 and 17-19, the first mould portion (1) can comprise a first tongue (10) which projects from the edge of the first half-shell (2), and the second mould portion (3) can comprise a second tongue (11) which projects from the edge of the second half-shell (4). The first tongue (10) and the second tongue (11) are arranged and conformed to be counter-faced with respect to each other when the first mould portion (1) and the second mould portion (3) are coupled together, and the fixing means (6) fix the first mould portion (1) and the second mould portion (3) removably with respect to each other at the first tongue (10) and the second tongue (11).

According to the embodiments shown in figures, the first tongue (10) can develop along the whole edge of the first half-shell (2) as well as the second tongue (11) can develop along the whole edge of the second half-shell (4) (see FIGS. 5-8 and 17-19).

Advantageously the fixing means (6) have a greater surface, they can work on.

Said fixing means (6) can be very simple as a system of screws and bolts. Preferably, said fixing means (6) comprise a first plate (12) conformed to be in contact to the first tongue (10), a second plate (13) conformed to be in contact to the second tongue (11) and a fixing element (14) (for example a system of screw and bolt) for fixing the first plate (12) and the second plate (13) with respect to each other, so that said first plate (12) and second plate (13) fix the first mould portion (1) and the second mould portion (3) with respect to each other.

According to the embodiments shown in figures, the first plate (12) and the second plate (13) can be conformed so that they touch entirely the first tongue (10) and the second tongue (11). Such feature, combined with the fact that the first tongue (10) and second tongue (11) can develop along the whole edge of the first half-shell (2) and second half-shell (4), allows an optimal seal of the first mould portion (1) and second mould portion (3): in this way, the fluid (preferably viscous) material injected in the opening (5c) is optimally compacted in the chamber (5), and as a consequence the mechanical performances of the temporary prosthesis of hip or shoulder further improve.

Moreover, also in case the first mould portion (1) and the second mould portion (3) are realized in a not rigid material (for example, the first mould portion (1) and the second mould portion (3) can be in polyethylene), such embodiment guarantees that a temporary prosthesis with good mechanical performances is obtained.

Preferably, the first tongue (10) and the second tongue (11) are connected with respect to each other so that the first mould portion (1) and the second mould portion (3) conform a unique body together (FIGS. 5-8 and 17-19). Therefore, the first mould portion (1) and the second mould portion (3) are mutually coupled as a book.

The first mould portion (1) and the second mould portion (3) can be realized by thermoforming. Preferably, the first mould portion (1) and the second mould portion (3) are disposable.

Similarly, the first plate (12) and the second plate (13) as well can be connected between each other so that they are coupled as a book (FIGS. 1-4 and 14-16).

Moreover, the supporting means (9) can be fixed to the first plate (12) and/or the second plate (13) (FIGS. 1-4 and 14-16).

The first insert (7) can be realized in polypropylene, silicone or polyethylene.

Preferably, the first insert (7) comprises a third tongue (15) which projects from the cap portion (8) and the head portion (5b) conforms a seat (16) to receive the third tongue (15) so that the cap portion (8) has a pre-set orientation and position in the head portion (5b) (see FIGS. 9-12 and 20-23).

Advantageously, the third tongue (15) guarantees the correct orientation and positioning of the cap portion (8) in the chamber (5), thus guaranteeing an optimal result.

The first insert (7) has a spherical cap shape. In particular, the first insert (7) has a spherical cap shape with a surface smaller than a semi-sphere. Advantageously, after solidification (more in detail, crosslinking) of the fluid (preferably viscous) material, the first insert (7) can be removed easily from the temporary prosthesis of hip or shoulder.

Preferably, the mould comprises a plurality of inserts comprising the first insert (7) and wherein each insert comprises a cap portion (8) which is realized as a unique body, which is dimensioned to be inserted in the head portion (5b) of the chamber (5), in contact to the first half-shell (2) and the second half-shell (4), and which is conformed to give shape to the head of the desired temporary prosthesis of hip or shoulder. The cap portion (8) of each insert of the plurality of inserts is dimensioned differently with respect to other cap portions so that, by changing insert, the dimension of the head of the desired temporary prosthesis of hip or shoulder can be set.

In particular, by changing the insert it is possible to vary the diameter of the head of the desired temporary prosthesis and the offset, i.e. the distance between the shaft axis and the head centre.

Advantageously, the mould is modular and has high flexibility. In fact, during the implantation surgical procedure of the temporary prosthesis, a surgeon can choose in loco (i.e. in operating room) the dimensions and the offset of the head of the desired temporary prosthesis.

Figure 24:
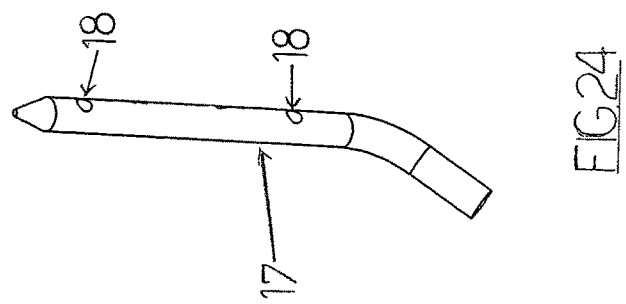
Figure 21:
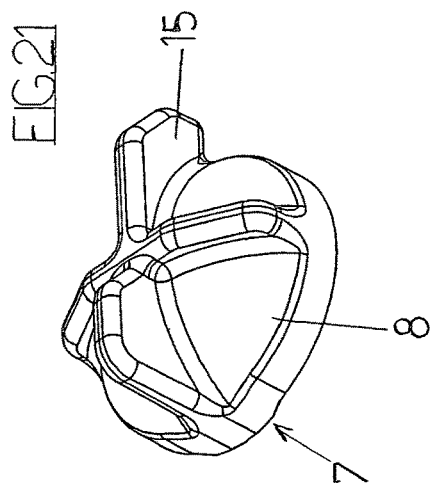
FIGS. 21 and 22 show a top perspective view and a top view of the insert of FIG. 20, respectively.
Figure 23:
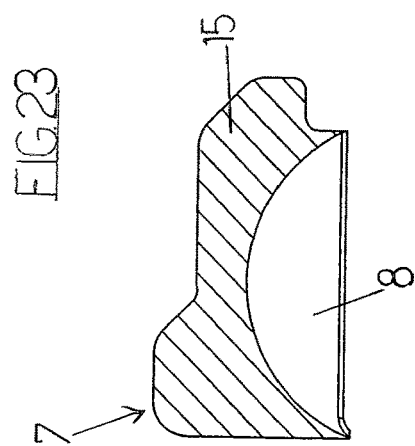
FIG. 23 shows section B-B of FIG. 22.
Figure 20:
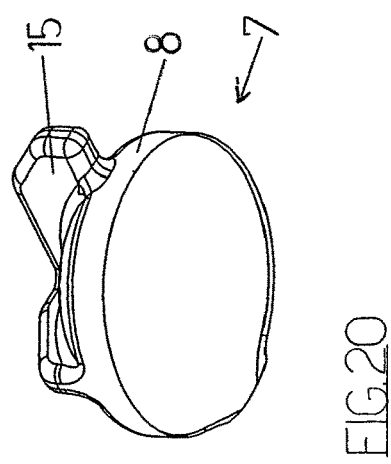
FIG. 20 shows a perspective view of another embodiment of the insert.
Figure 22:
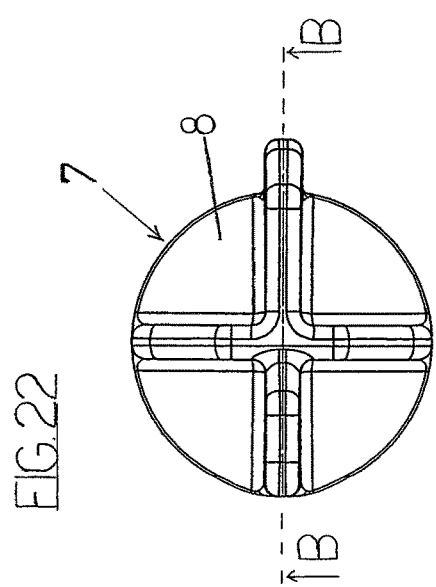

The mould can comprise also a stiffening element (17) (for example in metal material) which is arranged in the chamber (5) so that it is drowned in the fluid (preferably viscous; see FIGS. 13 and 24) material.

Said stiffening element (17) can comprise at least two through-holes (18) in which there can be introduced the supporting elements realized in a biocompatible material (for example, bone cement). The use of supporting elements makes the positioning of the stiffening element (17) in the chamber (5) easier and guarantees that the outer surface of the temporary prosthesis obtained with the mould is entirely in a not metal material so that it is avoided that parts in metal are exposed and can be contacted by the infected area.

The method object of the present invention for realizing a temporary prosthesis of hip or shoulder, provides the use of a mould according to any one of the above described embodiments and comprises the steps of: arranging the first insert (7) in the first half-shell (2) or in the second half-shell (4) and fixing the first mould portion (1) and the second mould portion (3) removably with respect to each other so that the cap portion (8) of the first insert (7) is inserted in the head portion (5b) of the chamber (5), in contact to the first half-shell (2) and the second half-shell (4); injecting a suitable fluid (preferably viscous) material in the opening (5c) for realizing a temporary prosthesis of hip or shoulder; after solidification of said fluid (preferably viscous) material, separating the first mould portion (1) and the second mould portion (3) and removing the first insert (7).

Preferably, the method comprises the steps of: arranging, before injecting the fluid (preferably viscous) material in the opening (5c), the first mould portion (1) and the second mould portion (3) so that the head portion (5b) is under the shaft portion (5a) (i.e. arranging the mould portion (1) and the second mould portion (3) vertically and pouring inside the viscous material); maintaining the first mould portion (1) and the second mould portion (3) in said position (vertically), in which the head portion (5b) is under the shaft portion (5a) until the solidification of the fluid (preferably viscous) material. Moreover, the step of injecting fluid (preferably viscous) material in the opening (5c) comprises the step of adjusting the quantity of fluid (preferably viscous) material injected, so that the length of the shaft of the desired temporary prosthesis of hip or shoulder is set.

Advantageously, there results greater flexibility since it is possible to adjust the length of the shaft of the temporary prosthesis of hip or shoulder and it is obtained a head of the temporary prosthesis which is compact (since it is the head portion (5b) the first to be filled with the fluid, preferably viscous material).

Moreover, in case the mould comprises a plurality of inserts, as above described, the method comprises the step of selecting, before fixing the first mould portion (1) and the second mould portion (3) removably with respect to each other, an insert among the plurality of inserts and of introducing said selected insert in the head portion (5b) for setting the dimension of the head of the desired temporary prosthesis of hip or shoulder.

Advantageously, it is possible to adjust the dimensions (diameter and offset) of the head of the temporary prosthesis of hip or shoulder.

The invention claimed is:

1. Mould for realizing a temporary prosthesis of hip or shoulder, which temporary prosthesis of hip or shoulder comprises a shaft and a head fixed to the shaft, wherein the mould comprises:
   a first mould portion (1) comprising a first half-shell (2);
   a second mould portion (3) comprising a second half-shell (4);
   the first mould portion (1) and the second mould portion (3) being able to be coupled with respect to each other so that, when coupled, the first half-shell (2) and the second half-shell (4) are counter-faced and define a chamber (5) which conforms a shaft portion (5a), a head portion (5b) and an opening (5c) for injection in the same chamber (5) of a suitable fluid material for a temporary prosthesis of hip or shoulder;

fixing means (6) for fixing the first mould portion (1) and the second mould portion (3) removably with respect to each other when the first mould portion (1) and the second mould portion (3) are coupled together;

a first insert (7) comprising a cap portion (8), which cap portion (8) is realized as a unique body, is dimensioned to be inserted in the head portion (5*b*) of the chamber (5), is in contact to the first half-shell (2) and the second half-shell (4), and is provided to give the shape to the head of the desired temporary prosthesis of hip or shoulder; and supporting means for supporting the first mould portion and the second mould portion when the first mould portion and the second mould portion are coupled together so that the head portion is under the shaft portion, so that by adjusting the quantity of fluid material injected in the opening it is possible to set the length of the shaft of the desired temporary prosthesis of hip or shoulder, wherein the head portion is interposed between the supporting means and the shaft portion in a longitudinal direction of the mould, wherein the first mould portion (1), the second mould portion (3) and the first insert (7) are mutually conformed to obtain a temporary prosthesis of hip or shoulder, when the first mould portion (1) and the second mould portion (3) are coupled together, the first insert (7) is inserted in the head portion (5) of the chamber (5) and the viscous material is injected in the opening (5*c*).

2. Mould according to claim 1, in which: the first mould portion (1) comprises a first tongue (10) which projects from an edge of the first half-shell (2); the second mould portion (3) comprises a second tongue (11) which projects from an edge of the second half-shell (4); the first tongue (10) and the second tongue (11) are arranged and conformed to be counter-faced with respect to each other when the first mould portion (1) and the second mould portion (3) are coupled together; the fixing means (6) fix the first mould portion (1) and the second mould portion (3) removably with respect to each other at the first tongue (10) and the second tongue (11).

3. Mould according to claim 2, wherein the fixing means (6) comprise a first plate (12) conformed to be in contact to the first tongue (10), a second plate (13) conformed to be in contact to the second tongue (11) and a fixing element (14) for fixing the first plate (12) and the second plate (13) with respect to each other so that said first plate (12) and second plate (13) fix the first mould portion (1) and the second mould portion (3) with respect to each other.

4. Mould according to claim 2, wherein the first tongue (10) and the second tongue (11) are connected with respect to each other so that the first mould portion (1) and the second mould portion (3) conform a unique body together.

5. Mould according to claim 1, in which: the first insert (7) comprises a tongue (15) which projects from the cap portion (8); the head portion (5*b*) conforms a seat (16) to receive the tongue (15) so that the cap portion (8) has a pre-set orientation and position in the head portion (5*b*).

6. Mould according to claim 1, comprising a plurality of inserts comprising the first insert (7) and wherein each insert comprises a cap portion (8) which is realized as a unique body, which is dimensioned to be inserted in the head portion (5*b*) of the chamber (5), in contact to the first half-shell (2) and the second half-shell (4), and which is conformed to give shape to the head of the temporary prosthesis of hip or shoulder; the cap portion (8) of each insert of the plurality of inserts is dimensioned differently with respect to other cap portions so that, by changing insert, the dimension of the head of the desired temporary prosthesis of hip or shoulder can be set.

7. Mould according to claim 2, in which: the first insert (7) comprises a third tongue (15) which projects from the cap portion (8); the head portion (5*b*) conforms a seat (16) to receive the third tongue (15) so that the cap portion (8) has a pre-set orientation and position in the head portion (5*b*).

8. Method for realizing a temporary prosthesis of hip or shoulder according to claim 1, comprising the steps of:

arranging the first insert (7) in the first half-shell (2) or in the second half-shell (4) and fixing the first mould portion (1) and the second mould portion (3) removably with respect to each other so that the cap portion (8) of the first insert (7) is inserted in the head portion (5*b*) of the chamber (5), in contact to the first half-shell (2) and the second half-shell (4);

injecting a suitable fluid material in the opening (5*c*) for realizing a temporary prosthesis of hip or shoulder;

after solidification of said fluid material, separating the first mould portion (1) and the second mould portion (3) and removing the first insert (7).

9. Method according to claim 8, comprising the steps of:

arranging, before injecting the fluid material in the opening (5*c*), the first mould portion (1) and the second mould portion (3) so that the head portion (5*b*) is under the shaft portion (5*a*);

maintaining the first mould portion (1) and the second mould portion (3) in said position, in which the head portion (5*b*) is under the shaft portion (5*a*), until the solidification of the fluid material;

wherein the step of injecting fluid material in the opening (5*c*) comprises the step of adjusting the quantity of fluid material injected so that the length of the shaft of the desired temporary prosthesis of hip or shoulder is set.

10. Method according to claim 8, wherein the mould comprises a plurality of inserts comprising the first insert (7) and wherein each insert comprises a cap portion (8) which is realized as a unique body, which is dimensioned to be inserted in the head portion (5*b*) of the chamber (5), in contact to the first half-shell (2) and the second half-shell (4), and which is conformed to give shape to the head of the temporary prosthesis of hip or shoulder; the cap portion (8) of each insert of the plurality of inserts is dimensioned differently with respect to other cap portions so that, by changing insert, the dimension of the head of the desired temporary prosthesis of hip or shoulder can be set and wherein the method comprises the step of selecting, before fixing the first mould portion (1) and the second mould portion (3) removably with respect to each other, an insert of the plurality of inserts and of introducing said selected insert in the head portion (5*b*) for setting the dimension of the head of the desired temporary prosthesis of hip or shoulder.

* * * * *